United States Patent [19]
Becht

[11] 4,207,898
[45] Jun. 17, 1980

[54] INTRALUMENAL ANASTOMOSIS SURGICAL STAPLING INSTRUMENT

[75] Inventor: Carl T. Becht, Cincinnati, Ohio

[73] Assignee: Senco Products, Inc., Cincinnati, Ohio

[21] Appl. No.: 890,262

[22] Filed: Mar. 27, 1978

[51] Int. Cl.² .................... A61B 17/04; A61B 17/32
[52] U.S. Cl. .................. 128/305; 128/334 R; 227/76
[58] Field of Search ............ 128/305, 334 R, 337, 128/346; 227/19, 76

[56] References Cited

U.S. PATENT DOCUMENTS

| | | | |
|---|---|---|---|
| 3,175,556 | 3/1965 | Wood et al. | 128/346 X |
| 3,252,643 | 5/1966 | Strekopytov et al. | 128/334 R |
| 3,552,626 | 1/1971 | Astafiev et al. | 227/19 X |
| 3,593,903 | 7/1971 | Astafiev et al. | 227/19 X |
| 3,692,224 | 9/1972 | Astafiev et al. | 227/19 |
| 3,822,818 | 7/1974 | Strekopytov et al. | 227/19 X |
| 4,047,654 | 9/1977 | Alvarado | 227/19 |

*Primary Examiner*—Robert W. Michell
*Assistant Examiner*—Michael H. Thaler
*Attorney, Agent, or Firm*—Frost & Jacobs

[57] ABSTRACT

A surgical stapling instrument for the joining together of tubular body organs. The instrument comprises an elongated cylindrical body supporting at its distal end a staple carrier containing at least one annular array of staples, a staple driver for each array and a cylindrical scalpel. A conical anvil is located beyond the staple carrier at the distal end of the instrument body and carries an annular anvil plate for clinching the staples of the one or more arrays thereof. The anvil has an elongated shank extending within the instrument body. The anvil and its shank are shiftable axially of the instrument body by an anvil drive screw at the proximal end of the instrument between a position wherein the anvil plate is adjacent the staple carrier and a position wherein the anvil plate is spaced from the staple carrier. An elongated hollow staple driver actuator is located within the instrument body, surrounding the anvil shank and is axially shiftable between a retracted position and a staple driving position by a staple drive wheel located at the proximal end of the instrument. An elongated hollow scalpel actuator is located within the instrument body surrounding the staple driver actuator and is axially shiftable between a retracted position and a scalpel driving position by a scalpel drive wheel at the proximal end of the instrument. A series of latch means are provided so that the various components of the instrument, during the anastomosis steps, can be operated only at the proper time and in the proper sequence.

17 Claims, 16 Drawing Figures

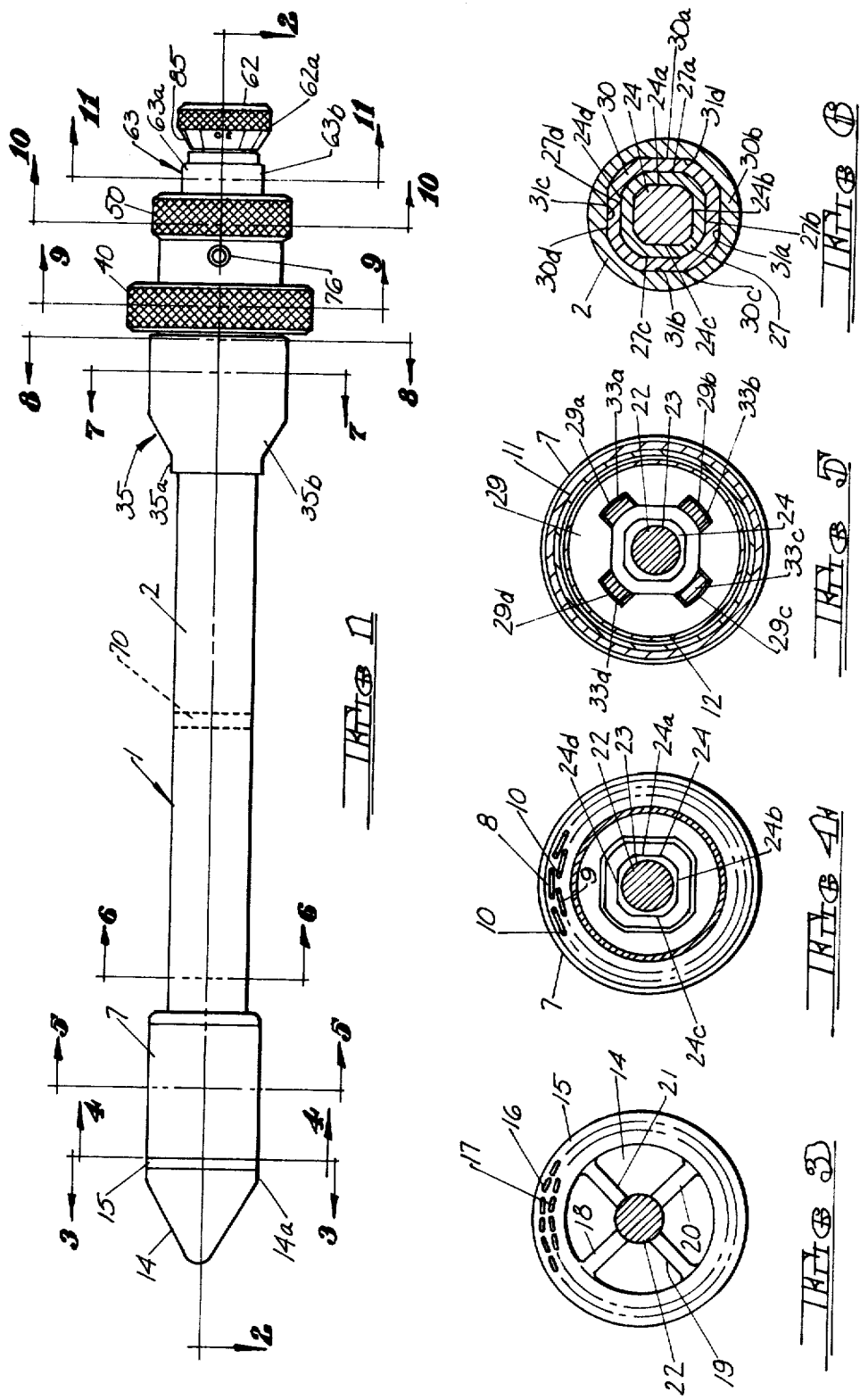

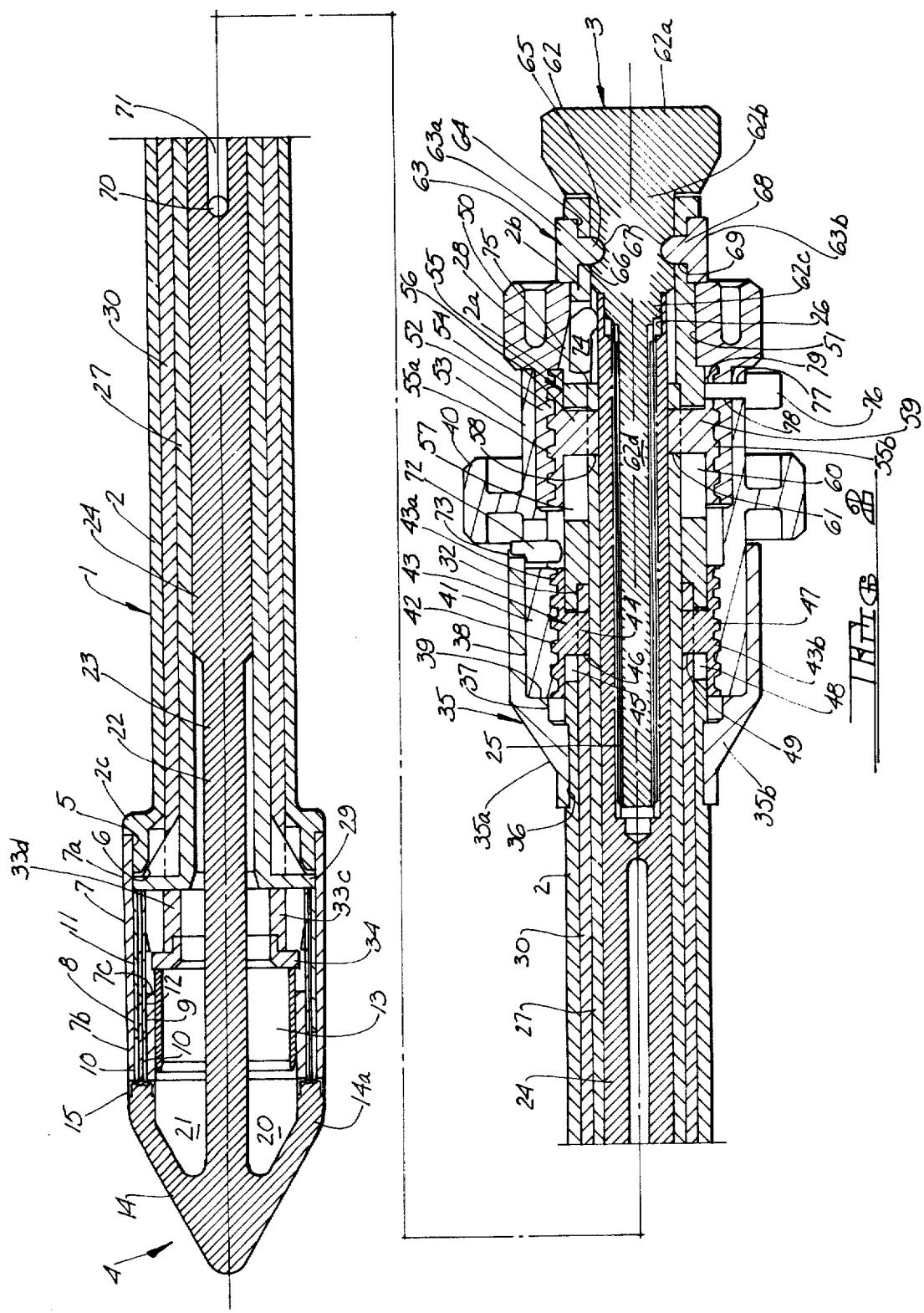

INTRALUMENAL ANASTOMOSIS SURGICAL STAPLING INSTRUMENT

BACKGROUND OF THE INVENTION

1. Field of the Invention

The invention relates to a surgical stapling instrument, and more particularly to such an instrument for the joining together of tubular body organs.

2. Description of the Prior Art

The most common surgical method of joining two tubular body parts has involved the use of conventional thread sutures. This is, however, a difficult and time-consuming procedure. To avoid this, prior art workers have turned to other expedients such as clamping means of the type shown in U.S. Pat. No. 2,453,056. More recently, considerable interest has centered around the use of staples to join tubular body parts since this is an easier procedure and of even greater importance, is very much faster. It will be understood that the less time required for suturing, the shorter the length of time the patient must be maintained under anesthesia.

One approach has been to join the tubular body parts in end-to-end relationship by stapling means which engage the body parts externally. This is illustrated in U.S. Pat. Nos. 2,940,451 and 3,606,888. Another approach involved the joining of overlapped tubular body parts as taught in U.S. Pat. No. 3,638,652. Yet another approach again joined the tubular body parts substantially in end-to-end relationship, engaging the tubular parts internally and removing excess portions of the tubular parts adjacent the line or lines of staples through the use of a cylindrical scalpel or the like. Such stapling devices are taught and illustrated in U.S. Pat. Nos. 3,193,165; 3,388,847; 3,552,626 and 3,593,903. These last mentioned patents teach surgical instruments having a pistol grip and being actuated by trigger means.

The present invention is directed to an intralumenal anastomosis medical stapling device more nearly like those of the last mentioned patents, but free of laterally extending protrusions, grips or triggers. The surgical instrument of the present invention possesses a number of advantages not found in the prior art. For example, the staple suture line is placed by the instrument independently of the cutting action of the cylindrical scalpel. The unique driving mechanism of the instrument enables the instrument to be virtually symmetrical about its axis and makes it practical to provide two or more concentric staple suture lines. Means are provided to prevent over-forming or crushing of the staple sutures irrespective of the force used by the surgeon.

A first latch means is provided to assure that all of the parts are in their proper position during initial insertion and positioning of the instrument. A second latch means guarantees that the staple suture line cannot be implanted unless the gap between the staple carrier and the anvil plate is within the forming limits of the staples. Yet a third latch means assures that the circular scalpel cannot be actuated until the staple suture line is fully implanted and properly crimped. As a result of this, the instrument is sequentially controlled and can only be used correctly by the surgeon, eliminating chance of human error.

The construction of the instrument lends itself well to the use of low cost materials, such as plastic or the like, making it practical to construct the instrument as a single-use, disposable instrument. The construction of the instrument further lends itself to the employment of a single-use, disposable staple carrier and/or the use of a single-use, disposable anvil plate. When the balance of the instrument is intended to be reusable, it may be made of durable material appropriate for use in a surgical environment and capable of withstanding sterilization procedures, such as stainless steel or the like. Finally, the particular configuration of the staple driver actuator and the anvil shank will assure proper radial alignment of the anvil plate and the staple carrier, preventing irregular formation of the staple sutures.

SUMMARY OF THE INVENTION

The surgical stapling instrument of the present invention is intended to join together (anastomose) disconnected tubular body structures. The instrument has an elongated cylindrical body, to the distal end of which is appropriately mounted a staple carrier. The staple carrier contains at least one annular array of staples, a staple driver for each annular array of staples and a cylindrical scalpel.

The instrument is provided with a conical anvil, ahead of the stapel carrier, and constituting a nose portion for the instrument enabling the instrument to be more easily inserted into the tubular body parts to be joined. The rearward portion of the anvil carries an anvil plate provided with staple clinching grooves. The anvil has an elongated shank extending into the instrument body. The anvil and the shank are shiftable axially of the body by an anvil drive screw at the proximal end of the instrument, between a retracted position wherein the anvil plate lies adjacent the staple carrier and an extended position wherein the anvil plate is spaced from the staple carrier.

An elongated hollow staple driver actuator is located within the instrument body, surrounding the anvil shank. The staple driver actuator is axially shiftable within the body of the instrument by a staple drive wheel at the proximal end of the instrument between a retracted position and an extended staple driving position.

In similar fashion, an elongated hollow scalpel actuator is located within the instrument body and surrounds the staple driver actuator. The scalpel actuator is axially shiftable within the instrument body by a scalpel drive wheel at the proximal end of the instrument body between a retracted position and an extended scalpel driving position.

A safety locking pin is provided to assure that the staple driver actuator and scalpel actuator are in their retracted positions during insertion of the tool into the tubular body members to be joined. Upon proper insertion and positioning of the instrument, the safety locking pin may be removed. A first latch means is provided preventing shifting of the staple driver actuator from its retracted position until the tubular body parts to be joined have been appropriately attached to the anvil shank (as will be described hereinafter) and the anvil plate has been returned to a position within the forming limits of the staples. Thus, the staples cannot be implanted in the tubular body parts to be joined unless proper crimping of the staples is assured.

A second latch means is provided preventing shifting of the scalpel actuator to its extended position until the staples have been properly implanted and clinched.

The anastomosis step is accomplished by inserting the instrument into a first one of the tubular body parts to be joined. This can be accomplished in one of three basic ways. First of all, a small incision may be made in the side of the first tubular body part a distance from its free or disconnected end. The instrument is then inserted through the incision and into the interior of the first tubular body part. If the tubular body parts to be joined are in the lower abdominal area, the instrument may be inserted into the first of the tubular body parts by means of a rectal approach. In similar fashion, if the tubular body parts to be joined are in the area of the esophagus, it would be practical to insert the instrument into the first tubular body part orally.

After the device has been inserted into the first of the tubular body parts to be joined, the anvil portion is adjusted so that it is a suitable distance from the staple carrier. With the device in this position, the free end of the first tubular body part is pulled around the end of the staple carrier and tied about the shank of the anvil in any appropriate manner. This may be accomplished, for example, by placing a continuous running suture around the periphery of the tubular body part and pulling it tight about the anvil shank.

The other tubular body part is similarly brought about the conical anvil and tied to the anvil shank. The anvil portion is then adjusted so that it is a suitable distance from the staple carrier (depending upon the staple being used, the thickness of the tubular body parts being joined and the condition of the tissue).

With the anvil and its anvil plate properly located with respect to the staple carrier, the staples are implanted and clinched to join the tubular body parts. Thereafter, the cylindrical scalpel is forced out of the staple carrier and through those portions of the tubular body parts tied to the shank of the anvil, thereby making a circular opening inside the joined tubular body parts. The anvil and its anvil plate are then shifted away from the staple carrier a short distance to release the joined body parts and the device is removed from the interior of the body parts, the anastomosis thereof being complete.

BRIEF DESCRIPTION OF THE DRAWINGS

FIG. 1 is a side elevational view of the surgical stapling instrument of the present invention with its various parts in their respective positions when the device is ready for use in surgery.

FIG. 2 is a cross sectional view taken along section 2—2 of FIG. 1.

FIG. 3 is a cross sectional view taken along section line 3—3 of FIG. 1.

FIG. 4 is a cross sectional view taken along section line 4—4 of FIG. 1.

FIG. 5 is a cross sectional view taken along section line 5—5 of FIG. 1.

FIG. 6 is a cross sectional view taken along section line 6—6 of FIG. 1.

DESCRIPTION OF THE PREFERRED EMBODIMENTS

Figures 7, 8:
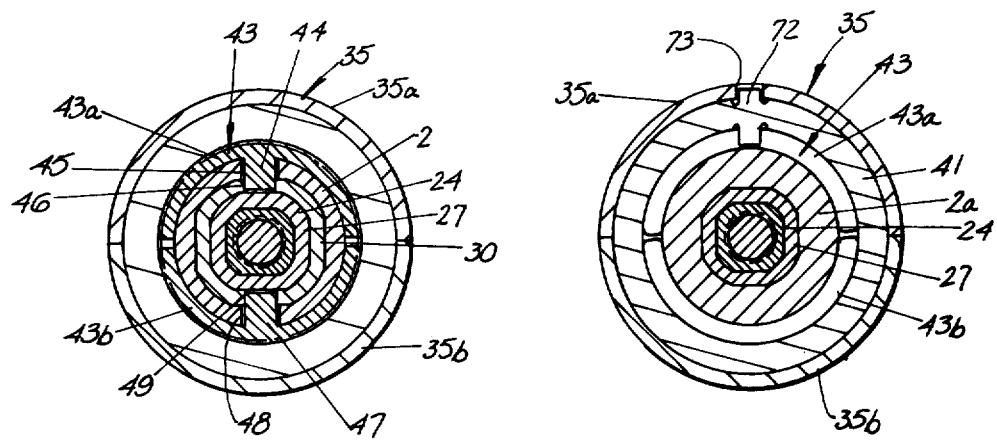
FIG. 7 is a cross sectional view taken along section line 7—7 of FIG. 1.
FIG. 8 is a cross sectional view taken along section line 8—8 of FIG. 1.

Throughout the Figures, like parts have been given like index numerals. Reference is first made to FIGS. 1 and 2. FIG. 1 is an elevational view of the surgical instrument of the present invention, generally indicated at 1, and FIG. 2 is a cross sectional view taken along section line 2—2 of FIG. 1. Both of these figures illustrate the surgical instrument with its various parts in the positions they will occupy when the instrument is ready for use in surgery. The instrument comprises an elongated tubular or cylindrical body 2. Near the proximal end of the instrument (generally indicated at 3) the external diameter of the body 2 remains constant, but the body 2 has a portion 2a of increased wall thickness. A final portion 2b of the body 2 increases, again in thickness, providing another slight diminishing of the internal dimension.

Near the distal end of the instrument 1 (generally indicated at 4) the body 2 has an enlarged cylindrical portion 2c of increased internal and external dimensions. The end of the body portion 2c is provided with an exterior annular notch 5 and is relieved interiorly as at 6.

A hollow staple carrier 7 is affixed to the distal end of the instrument body. The staple carrier 7 is of circular cross section and its exterior surface may taper slightly toward the distal end of the instrument, as shown in the figure. The proximal portion 7a of the staple carrier 7 has an interior diameter permitting it to be just nicely received within the annular notch 5 at the distal end of the instrument body portion 2c. The staple carrier 7 may be attached to the body portion 2c in any appropriate way depending upon the material from which these elements are made and depending upon whether the entire instrument or just the staple carrier is intended to be disposable.

The distal portion 7b of the staple carrier has a lesser interior diameter, forming a shoulder 7c between staple carrier portions 7a and 7b.

The instrument of the present invention may readily be designed to implant one or more circular arrays of surgical staples. For purposes of an exemplary showing, the instrument will be illustrated and described in terms of the presence of two circular arrays of surgical staples. To this end, the distal portion 7b of staple carrier 7 is provided with a first circular arrangement of longitudinal slots 8 and a second circular array of longitudinal slots 9 (see FIG. 4). Each of the slots 8 is intended to house a surgical staple 10 and one leg of a cylindrical staple driver 11 (see also FIG. 5). In similar fashion, each longitudinal slot 9 in the portion 7b of staple carrier 7 is intended to house a surgical staple 10 and one leg of a cylindrical staple driver 12. It will be understood that the proximal portions of staple drivers 11 and 12 constitute cylindrical elements, the distal ends of which are divided up into legs equal in number to the number of longitudinal slots 8 and 9 in the portion 7b of staple carrier 7. Finally, a cylindrical scalpel 13 is maintained in position within the staple carrier portion 7b by a frictional fit.

Turning next to FIGS. 1, 2 and 3, a conical anvil 14 is provided at the distal end of the instrument. The anvil 14 is preferably conical shaped to assist in the insertion of the instrument in the tubular body parts to be joined. The rearward or proximal end of the anvil 14 is in the form of an annular skirt 14a supporting an annular anvil plate 15. The anvil plate 15 has a first annular array of staple clinching grooves 16 adapted to cooperate with the outermost annular array of staples 10. A second annular array of staple clinching grooves is shown at 17 to cooperate with the innermost annular array of staples 10.

The anvil 14 is hollow and provided with reinforcing ribs 18 through 21 extending radially from a shank 22. The shank 22 has a first portion 23 of circular cross section and a second portion 24 again of circular cross section, but of larger diameter and having four longitudinal flats 24a through 24d formed thereon. This is most clearly shown in FIGS. 4 and 6.

At its proximal end, the shank portion 24 of the anvil shank 22 is provided with an internally threaded bore 25. This bore terminates at the proximal end of shank portion 24 in a larger, unthreaded bore 26. The purpose of bores 25 and 26 will be described hereinafter.

Mounted within the body 2 of the instrument and surrouding the shank 22 of anvil 14 there is an elongated, tubular staple driver actuator 27. As is most clearly seen in FIG. 6, the staple driver actuator 27 is a tubular member having an internal diameter equivalent to the external diameter of the portion 24 of anvil shank 22. The staple driver actuator is also provided with flats 27a through 27d corresponding the the flats 24a through 24d of the anvil shank portion 24. The staple driver actuator 27 is slidable axially with respect to anvil shank 22 but the two are not rotatable with respect to each other. In FIGS. 1 and 2, the staple driver actuator 27 is shown in its fully retracted position. This position is determined by abutment of the proximal end of the staple driver actuator 27 against the interior shoulder 28 formed between the portions 2a and 2b of the instrument body 2. At its distal end, the staple driver actuator 27 terminates in an annular driver member 29 most clearly shown in FIG. 5. The driver member 29 is intended to engage the proximal ends of staple drivers 11 and 12 (see FIGS. 2 and 5) so that when the staple driver actuator 27 is shifted toward the distal end of the instrument, it will drive the staples 10, as will be described hereinafter. The driver member 29 is provided with four openings 29a through 29d to accommodate a portion of the scalpel actuator next to be described.

The scalpel actuator is shown at 30 and comprises an elongated tubular member surrounding the staple driver actuator 27. Turning again to FIG. 6, it will be noted that the scalpel driver 30 is again provided with a series of flats 30a through 30d correspodnding to the flats 24a through 24d of the anvil shank portion 24 and the flats 27a through 27d of the staple driver actuator 27. It will also be noted from FIG. 6 that the interior surface of the instrument body 2 is provided with a cooperating series of flats indicated at 31a through 31d. The scalpel actuator 30 is axially shiftable with respect to the instrument body 2 and the staple driver actuator 27, and is non-rotatable with respect to both. At this point it will be evident that the shank 22 of anvil 14, the staple driver actuator 27 and the scalpel actuator 30 are all axially shiftable within the instrument body 2, but are non-rotatable therein. Thus, proper alignment will always be maintained between the staples 10 and the staple clinching grooves 16 and 17 of anvil plate 15. The scalpel actuator 30 is illustrated in FIG. 2 in its fully retracted position which is determined by the abutment of its proximal end with the shoulder 32 formed between the central portion of the instrument body 2 and that portion 2a of instrument body 2. At its distal end, the scalpel actuator 30 terminates in four legs 33a through 33d adapted to pass with a sliding fit through the openings 29a through 29d, respectively, in the driver member 29 of staple driver actuator 27. The free ends of legs 33a through 33d support an annular scalpel driver 34 adapted to engage the rearward end of the cylindrical scalpel 13 and shift the scalpel 13 to its cutting position when the scalpel actuator 30 is shifted toward the distal end of the instrument 1, as will be described hereinafter. All of the actuating means to cause axial shifting of the anvil 14, the staple driver actuator 27 and the scalpel actuator 30 are located at the proximal end of the instrument 1 and will next be described.

The instrument 1 is provided near its proximal end with a split collar generally indicated at 35. The collar 35 is made up of two halves 35a and 35b as can most clearly be seen in FIGS. 1 and 7. The base of the collar 35 fits within an annular recess 36 in the instrument body 2. The collar 35 may be affixed to the instrument body 2 in any suitable manner. The collar 35 has a first portion 37 having an internal diameter greater than the external diameter of the instrument body 2. The collar has a second portion 38 of an even greater internal diameter forming a shoulder 39 between it and collar portion 37.

A scalpel drive wheel 40 is rotatably mounted on the instrument body 2. The scalpel drive wheel 40 has a cylindrical portion 41 located beneath the portion 38 of split collar 35 and abutting the shoulder 39 thereof. The portion 41 of scalpel drive wheel 40 is internally threaded as at 42.

Surrounding the body 2 of the instrument and in threaded engagement with the portion 41 of scalpel drive wheel 40 there is a split nut generally indicated at 43 and made up of halves 43a and 43b (see also FIG. 7). The split nut half 43a has an inwardly extending lug 44 passing through a slot 45 in the instrument body 2 and into a perforation 46 in the proximal end of the scalpel actuator 30. In similar fashion, the split nut half 43b has an inwardly extending lug 47 passing through a slot 48 in instrument body 2 and into a perforation 49 located in the proximal end of the scalpel actuator 30 diametrically opposite the perforation 46. It will be evident from FIG. 2 that when the scalpel drive wheel 40 is turned in one direction, the threaded engagement between the scalpel drive wheel portion 41 and the split nut 43 will cause the scalpel actuator 30 to shift toward the distal end of the instrument. Similarly, opposite rotation of scalpel drive wheel 40 will cause the scalpel actuator 30 to shift toward the proximal end of the instrument.

A staple drive wheel is shown at 50. The staple drive wheel 50 is rotatably mounted in an annular external notch 51 in the portion 2b of the instrument body 2. The staple drive wheel 50 has a cylindrical portion 52 which underlies a cylindrical portion 53 of the scalpel drive wheel 40. Abutment of the scalpel drive wheel portion 41 against the split collar shoulder 39 at one end and abutment of the scalpel drive wheel portion 53 against the staple drive wheel 50 prevents axial movement of the scalpel drive wheel 40. The abutment of the scalpel drive wheel portion 53 against the staple drive wheel 50 also precludes any tendency of the staple drive wheel 50 to shift axially toward the distal end of the instrument 1.

Figure 9:
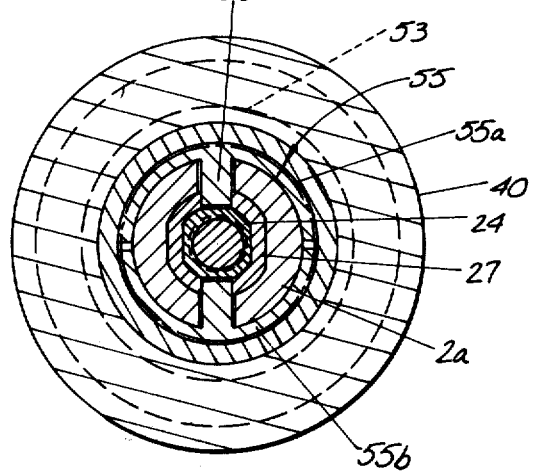
FIG. 9 is a cross sectional view taken along section line 9—9 of FIG. 1.

The cylindrial portion 52 of the staple drive wheel 50 is internally threaded as at 54. The internal threads 54 are engaged by a split nut generally indicated at 55 and made up of a first half 55a and a second half 55b (see also FIG. 9). The split nut half 55a has an inwardly extending lug 56 which passes through a slot 57 in the instrument body portion 2a and a perforation 58 in the proximal end of the staple driver actuator 27. In similar fashion, the split nut half 55b is provided with an inwardly extending lug 59 passing through a slot 60 in the instrument body portion 2a, diametrically opposed to the slot 57. The lug 59 also extends into a perforation 61 in the distal end of the staple driver actuator 27, diametrically opposite the perforation 58. It will now be evident that when the staple drive wheel is turned in one direction, the interaction of the split nut 55 with the internal threads 54 of staple drive wheel portion 52 will result in a shifting of the staple driver actuator 27 toward the distal end of the instrument. The opposite rotation of the staple drive wheel 50 will result in opposite axial movement of the staple driver actuator 27.

Axial shifting of the anvil 14 is accomplished by the interaction of the proximal end of the anvil shank 22 and an anvil drive screw 62. The anvil drive screw 62 has a knob-like portion 62a followed by a first cylindrical portion 62b, a second cylindrical portion 62c and an elongated threaded portion 62d. The threaded portion 62d engages the internally threaded bore 25 at the proximal end of the anvil shank 22. The cylindrical portion 62c of the anvil drive screw is intended to be received within the anvil shank bore 26 with a slight interference fit, the reason for which will be described hereinafter. The cylindrical portion 62b of the anvil drive screw 62 is received in the proximal end of the instrument body portion 2b and is rotatable therein.

Figures 10, 11:
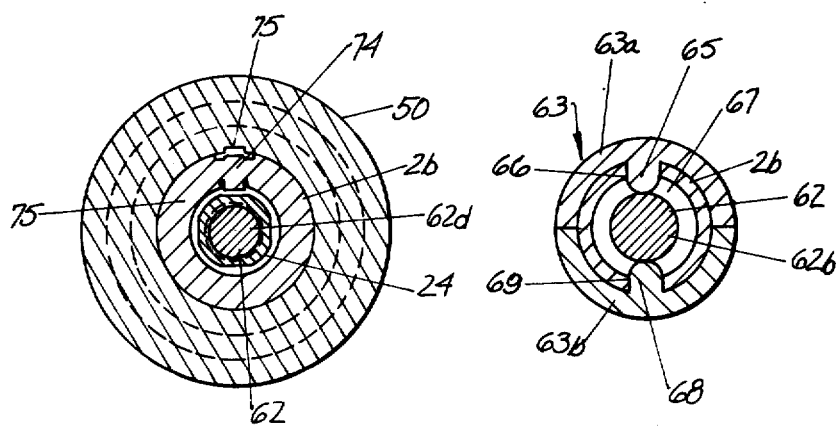
FIG. 10 is a cross sectional view taken along section line 10—10 of FIG. 1.
FIG. 11 is a cross sectional view taken along section line 11—11 of FIG. 1.

The anvil drive screw is held against axial movement by means of a split collar generally indicated at 63. The collar is made up of two halves 63a and 63b appropriately affixed to the body portion 2b of the instrument body 2 in an annular notch 64 therein. The split collar half 63a is provided with an inwardly extending lug 65 passing through a perforation 66 in the body portion 2b of the instrument body 2 and into an annular notch 67 in the portion 62b of the anvil drive screw 62. In similar fashion, the split collar half 63b is provided with an inwardly extending lug 68 passing through a perforation 69 in the portion 2b of the instrument body, 2, diametrically opposite the perforation 66. The lug 68 also enters the annular notch 67 in the portion 62b of the anvil drive screw 62. The engagement of the anvil drive screw 62 by the lugs 65 and 68 of split collar 63 is clearly shown in FIG. 11.

It will be evident from the above that when the anvil drive screw is turned in one direction, the interaction of the drive screw threaded portion 62d and the threaded bore 25 of the anvil shank 22 will cause the anvil 14 to shift away from staple carrier 7. Opposite rotation of the anvil screw 62 will return the anvil to the position shown in FIG. 2. Split collar 63 also abuts the proximal end of staple drive wheel 50 preventing axial movement thereof toward the proximal end of instrument 1.

The instrument of the present invention is provided with a number of safety devices. First of all, a stop pin 70 (see FIGS. 1 and 2) extends transversely through the instrument body 2, being held in diametrically opposed perforations (not shown) in the instrument body by any suitable means including an interference fit. The stop pin 70 passes through a longitudinal slot 71 in the portion 24 of anvil shank 22 and corresponding slots, not shown, in staple driver actuator 27 and scalpel actuator 30. The primary purpose of stop pin 70 is to prevent unintentional disassembly of the instrument 1 (i.e. disengagement of anvil drive screw portion 62d from threaded anvil shank bore 25) while it is in use.

Reference is now made to FIGS. 2 and 8. The portion 41 of scalpel drive wheel 40 has in association with it a resiliently mounted latch 72 which normally engages a notch 73 in the portion 38 of split collar 35. The latch 72 may be pivotally mounted to the portion 41 of scalpel drive wheel 40 and spring biased, or it may be an integral, resilient, shiftable part of the scalpel drive wheel portion 41, as illustrated. The latch 72 when engaged in the notch 73 of split collar 35 will inhibit rotation of the scalpel drive wheel 40 until it is shifted out of the notch 73 by being engaged by split nut half 55a, as will be described hereinafter.

A somewhat similar latch 74 is located in the portion 2b of the instrument body 2. The latch 74 may be of the same type described with respect to the latch 72, constituting a separate spring biased element or a resilient, integral part of instrument body portion 2b. The latch 74 is biased to enter a slot 75 in staple drive wheel 50, precluding rotation of the staple drive wheel 50, unless removed from the notch 75 by the proximal end of shank portion 24 of anvil 14. The latch 74 will be contacted and shifted out of the slot 75 by the proximal end of the shank portion 24 of anvil 14 (permitting rotation of staple drive wheel 50) whenever the anvil 14 and its anvil plate 15 is spaced from staple carrier 7 by a distance within the forming limits of the staples 10. As a consequence, if anvil plate 15 is not sufficiently close to the staple carrier 7 to permit forming or clinching of the staples 10 by the anvil plate staple clinching grooves 16 or 17, the staples cannot be driven.

Finally, a third latch in the form of a safety pin 76 is provided. The pin 76 is illustrated in FIGS. 1 and 2. As is most clearly shown in FIG. 2, the safety pin 76 is adapted to extend through a perforation 77 in scalpel drive wheel portion 53, a perforation 78 in staple drive wheel portion 52 and a perforation 79 in split nut half 55b. The safety pin 76 is used to assure that the staple driver actuator 27 and the scalpel actuator 30 are in their proper positions during insertion of the instrument into the tubular body parts to be joined and the setting of a proper gap between anvil plate 15 and staple carrier 7, all of which will next be described.

The operation of the surgical stapling instrument 1 of the present invention will, for purposes of an exemplary showing, be described in its use to provide the required anastomosis during a lower anterior resection surgical procedure. The rectal approach for insertion of the device will be assumed to be indicated and it will further be assumed that excision of the desired segment of the lower colon has been accomplished.

Figure 14:
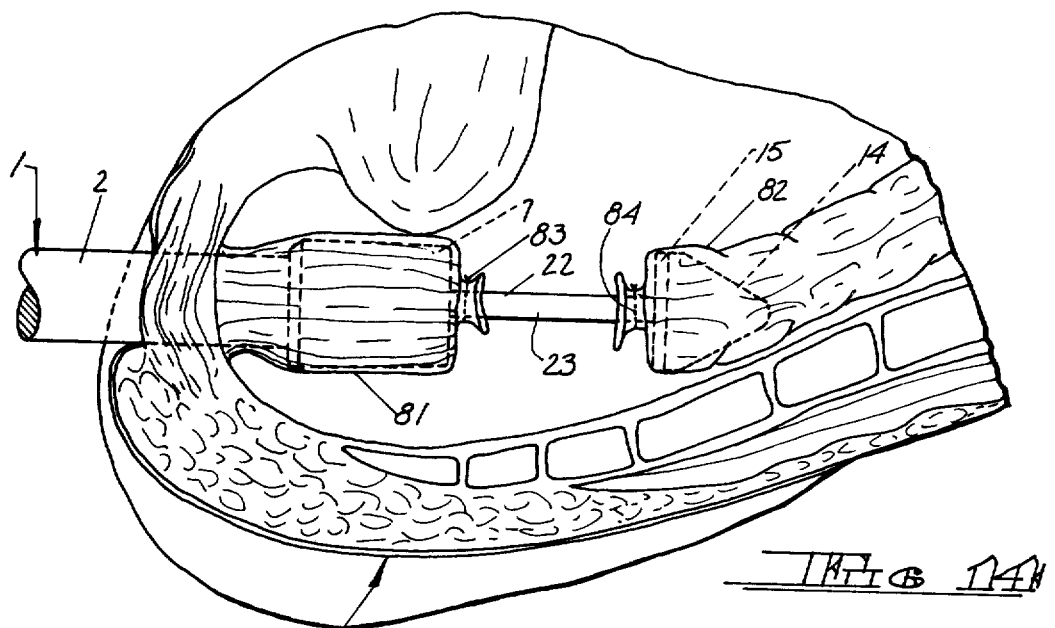
FIG. 14 is a fragmentary cross sectional view illustrating the manner of use of the surgical stapling instrument during anastomosis in a lower anterior resection surgical procedure.

The component parts of the surgical stapling instrument 1 will initially be in their respective positions illustrated in FIGS. 1 and 2. After the excision of the appropriate segment of lower colon, the surgeon will place a continuous-running suture through the periphery of the lower end of the remaining colon and another continuous running suture through the periphery of the upper end of the remaining rectal stump. Reference is now made to FIG. 14 constituting a framentary cross sectional view of a human body, generally indicated at 80. The rectal stump is shown at 81 and the lower end of the colon is shown at 82. The instrument 1 is inserted through the rectum into the interior of the rectal stump 81. The safety pin 76 is preferably left in place during this process to avoid unintentional rotation of staple drive wheel 50. After the instrument 1 has been suitably located in the rectal stump 81, the anvil drive screw 62 is rotated so as to cause the anvil 14 and anvil plate 15 to move away from staple carrier 7 until the desired distance is achieved between the anvil plate 15 and the staple carrier 7, or until the stop pin 70 engages the proximal end of the slot 71 in the anvil shank portion 24.

Figure 12:
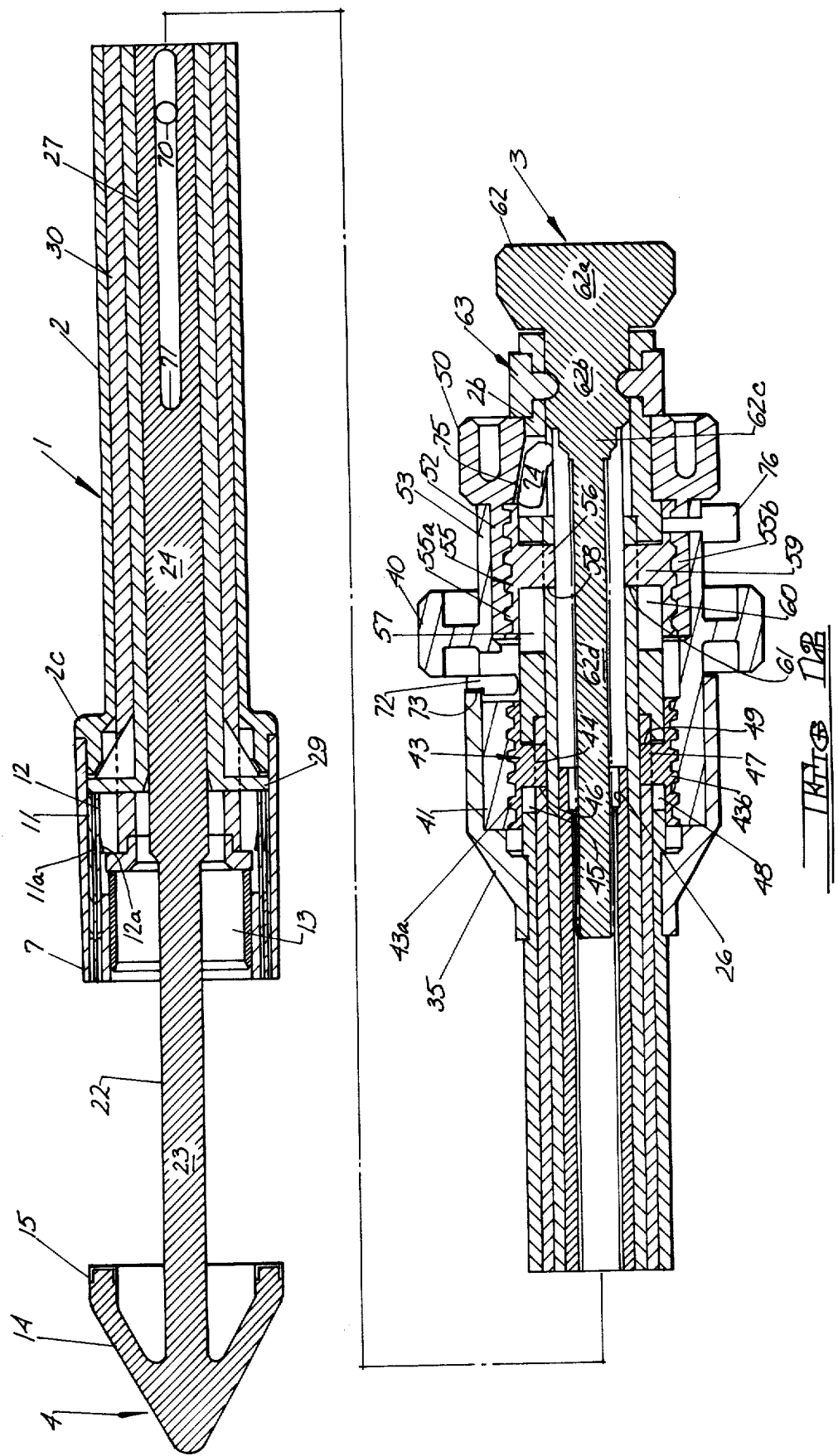
FIG. 12 is a cross sectional view similar to FIG. 2 but illustrating the anvil in its fully extended position.

The anvil 14 is shown in this extended position both in FIGS. 12 and 14. It should be noted in FIG. 12 that initial rotation of the anvil screw 62 advances the proximal end of anvil shank portion 24 so that it will now permit latch 74 to engage notch 75 in staple drive wheel 50. Thus, initial rotation of anvil screw 62 will cause latch 74 to lock staple drive wheel 50. Latch 72 normally locks scalpel drive wheel 40 against rotation and therefore, at this point, safety pin 76 may be removed if desired.

When the surgeon has advanced anvil 14 and anvil plate 15 the desired distance from staple carrier 7, he will then pull both ends of the continuous suture 83 running through the periphery of rectal stump 81 (FIG. 14), thereby tying the end of the rectal stump around the staple carrier 7 and to the cylindrical portion 23 of anvil shank 22. Thereafter, the lower end of the remaining colon is opened and placed over the anvil 14 and anvil plate 15. Again by pulling on both ends of the continuous-running suture 84 in the pheriphery of the end of the remaining colon 82, the colon end 82 is tied around the cylindrical portion 23 of anvil shank 22. The anvil drive screw 62 is now rotated in a direction causing the anvil 14 and anvil plate 15 to retract toward staple carrier 7. When the anvil 14 and its anvil plate 15 is positioned from staple carrier 7 by a distance equal to the maximum forming limits of staples 10, the proximal end of anvil shank portion 24 will have engaged the resilient latch 74 shifting it out of the slot 75 in the staple drive wheel. Substantially simultaneously with the disengagement of latch 74 from staple drive wheel 50, the cylindrical portion 62c of anvil drive screw 62 will enter bore 26 in the proximal end of anvil shank portion 24. Since the cylindrical portion 62c of anvil drive screw 62 has a slight interference fit in bore 26, the anvil drive screw will become noticeably more difficult for the surgeon to rotate, thus indicating to the surgeon that the anvil plate 15 is spaced from staple carrier 7 by the maximum forming limit of staples 10 and that it is time for him to set the desired gap between the anvil plate 15 and staple carrier 7 by means of calibrations about the periphery of anvil drive screw 62. Such calibrations are indicated at 85 in FIG. 1. The size of the gap between anvil plate 15 and staple carrier 7 will depend upon the nature, thickness and condition of the tissue of the rectal stump 81 and lower colon 82.

It is possible for the three above mentioned actions to take place simultaneously, or very nearly simultaneously. Thus, latch 74 could disengage from slot 75 in staple drive wheel 50 by virtue. of the shifting of the proximal end of shank portion 24 of anvil 14 at the same time that the desired gap is set by the surgeon and at the same time the cylindrical portion 62c of anvil drive screw 62 enters bore 26 at the distal end of shank portion 24 of anvil 14. These three actions will indeed occur substantially simultaneously if the desired gap is at or near the maximum gap within the forming range of staples 10. If a smaller gap is indicated, the surgeon will continue to turn anvil drive screw 62 until the desired gap is set, and latch 74 will have been shifted to its unlatching position, releasing staple drive wheel 50, and the cylindrical portion 62c of the anvil drive screw will enter further into the bore 26 of the anvil shank portion 24.

Once the desired gap has been set, it is then time to drive and clinch the staples 10 through the approximated portions of the rectal stump 81 and lower colon 82. If safety pin 76 has not previously been removed from the instrument 1, it must now be removed to enable rotation of the staple drive wheel 50. From the description thus far set forth it will be evident that even if the safety pin 76 had been removed after insertion and placement of the instrument 1 within the rectal stump 81 and lower colon 82, the staples 10 could not be driven until a gap within the maximum safe forming range of staples 10 had been achieved, by virtue of the interaction of staple drive wheel 50 and latch 74. Therefore, the instrument is sequentially controlled such that the staples 10 cannot be driven and clinched until it is assured that they will properly pass through the approximated portions of the rectal stump 81 and lower colon 82 and will indeed be adequately clinched.

Figure 13:
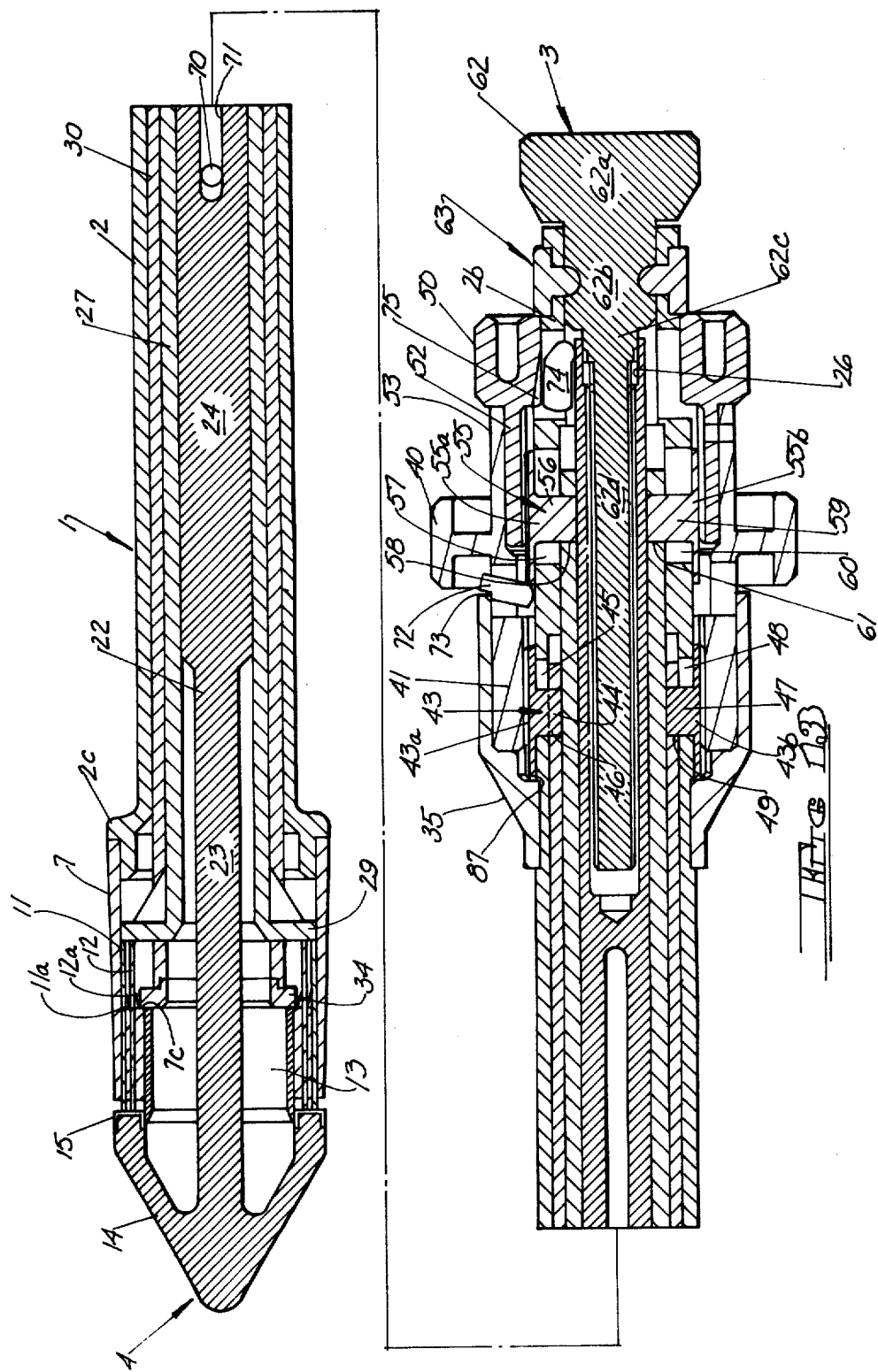
FIG. 13 is a cross sectional view, similar to FIG. 2 illustrating the staple driver actuator and the scalpel actuator in the extended positions they occupy after the completion of the anastomosis, but prior to removal of the device from the joined tubular body parts.
Figure 15:
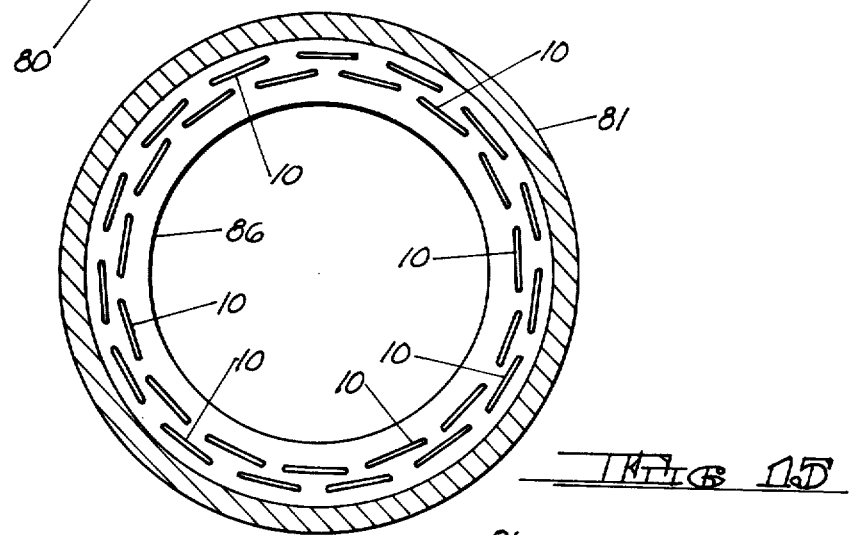
FIG. 15 is a cross sectional view illustrating a completed anastomosis.

To drive and clinch the staples 10, it is only necessary to rotate the staple drive wheel 50 in the proper direction. As taught above, this will (through the action of split screw 55) cause longitudinal shifting of staple drive actuator 27, shifting the staple drivers 11 and 12 toward the distal end of the instrument 1. The staples 10 will thus be driven through the approximated portions of the rectal stump 81 and lower colon 82 and will be clinched by the annular arrays of clinching grooves 16 and 17 in the anvil plate 15. In this way a double row of staple sutures are formed holding the rectal stump 81 to the lower colon 82. This is illustrated in FIG. 15. FIG. 13 illustrates the instrument 1 with the staple driver actuator 27 and staple drivers 11 and 12 in their staple driven positions. It will be noted from both FIGS. 2 and 13 that staple drivers 11 and 12 are provided with laterally upset tangs 11a and 12a. These tangs are provided to abut the shoulder 7c of staple carrier 7 to assure that staple drivers 11 and 12 will stop before so great a force is put upon the staples as to malform or crush them. This is true because when tangs 11a and 12a contact the shoulder 7c of staple carrier 7, further rotation of the staple driver actuator wheel 50 is prohibited. Tangs 11a and 12a are shown in contact with shoulder 7c in FIG. 13.

It is evident from FIG. 13 that shifting of the split screw 55 toward the distal end of the instrument 1 will result in shifting of latch 72 out of the notch 73 in split collar 35. This releases the scalpel driver wheel 40 for rotation. Here again, the instrument 1 is sequentially controlled so that the staples 10 must be securely in place before the circular scalpel 13 can be advanced. As described above, proper rotation of scalpel driver wheel 40 will advance the scalpel out of the staple carrier 7 toward the distal end of the instrument 1 and through the tissue of rectal stump 81 and lower colon 82 forming a clean circular passage therethrough, as shown at 86 in FIG. 15. FIG. 13 also illustrates the cylindrical scalpel 13 in its advanced position. The portions of the rectal stump 81 and lower colon 82 which were previously tied to the shank portion 23 of anvil 14 will thus be severed from the previously staple sutured rectal stump and colon so that they may be withdrawn therefrom together with the instrument. The surgeon will know that the cylindrical scalpel 13 has preformed its cutting operation when the split nut 43 abuts the inside surface of split collar 35 as is shown in FIG. 13 at 87.

At this point the anastomosis is complete and it is time to remove the instrument 1. In order to do this, the anvil drive screw 62 is rotated so as to cause the anvil 14 and anvil plate 15 to move away from the staple carrier 7. Only a slight movement (in the order of 0.5 centimeters) is required to release the sutured rectal stump and lower colon from between the anvil plate 15 and staple carrier 7. The instrument is thereafter removed by gently pulling it through the rectum. During the process of removing the instrument, the anastomosis will expand due to the elasticity of the tissue, thereby letting the distal end of the instrument 1 pass through the anastomosis.

As indicated above, the construction of the instrument 1 lends itself to the use of low cost materials, such as plastic, thereby making it practical to make the instrument 1 a single-use, disposable device. On the other hand, the instrument 1 may be made of more durable material such as stainless steel or the like, utilizing a disposable staple carrier 7. Anvil plate 15 may also be disposable, if desired.

Figure 16:
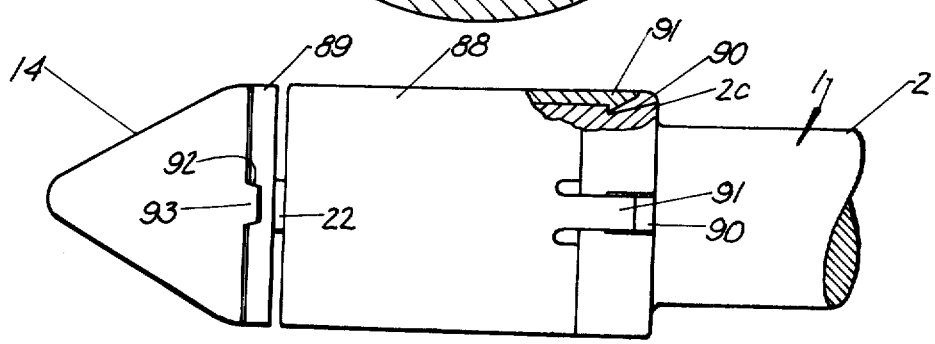
FIG. 16 is a fragmentary elevational view, partly in cross section, of the distal end of the instrument illustrating a disposable anvil plate and a disposable staple carrier.

Reference is made to FIG. 16 wherein the instrument 1 is illustrated as having a disposable staple carrier 88 and a disposable anvil plate 89. The instrument 1, itself, will be of the same construction as described with respect to FIGS. 1 and 2, with the exception that the portion 2c of the body 2 will be provided with two or more notches 90. The disposable staple carrier 88 will be of the same construction as described with respect to staple carrier 7 of FIGS. 1 and 2, with the exception that at its proximal end it will have resilient tines 91 equal in number to the number of notches 90 in body portion 2c. The times 91 will have a snap engagement with the notches 90, holding the disposable staple carrier 88 firmly in place.

The disposable anvil plate 89 will be provided with a series of staple clinching grooves identical to those shown at 16 and 17 in FIG. 3. The disposable anvil plate 89 may be affixed to anvil 14 in any suitable, detachable manner including the use of a frictional fit, latch means (not shown) or the like. Means should also be provided to assure that the disposable anvil plate 89 will have the proper radial position on anvil 14, with respect to the staple carrier 88, so that the staple clinching grooves therein will be properly aligned with the staples housed in staple carrier 88. One way of accomplishing this is to provide a notch 92 in the peripheral portion of disposable anvil plate 89, intended to receive a locating lug 93 formed on anvil 14.

Modifications may be made in the invention without departing from the spirit of it.

The embodiments of the invention in which an exclusive property or privilege is claimed are defined as follows:

1. A surgical stapling instrument for the joining together of tubular body organs, said instrument having distal and proximal ends, said instrument comprising an elongated body, a staple carrier mounted on said body near said distal end of said instrument, at least one annular array of staples together with a staple driver for said at least one array of staples and a cylindrical scalpel being located in said staple carrier, said instrument having a conical anvil located at said distal end of the instrument beyond said staple carrier, an annular anvil plate for clinching the staples of said at least one array, said anvil plate being mounted on said anvil facing said staple carrier, said anvil being axially shiftable between a first position wherein said anvil plate is adjacent said staple carrier and a second position wherein said anvil plate is spaced from said staple carrier, means to shift said anvil, a staple driver actuator located within said instrument body, said staple driver actuator being axially shiftable between a retracted position and a staple driving position wherein said staple driver actuator contacts and shifts said staple driver driving said at least one array of staples from said staple carrier and against said anvil plate, means to shift said staple driver actuator, a scalpel actuator located within said instrument body, said scalpel actuator being shiftable between a retracted position and a scalpel driving position wherein said scalpel actuator contacts and shifts said cylindrical scalpel partway out of said staple carrier toward said distal end of said instrument, means to shift said scalpel actuator and including means to control the sequence of actuation of said anvil shifting means, said staple driver actuator shifting means, and said scalpel actuator shifting means to assure proper sequential operation of said instrument.

2. The structure claimed in claim 1 including means to prevent unintentional disassembly of said instrument.

3. The structure claimed in claim 1 wherein said staple carrier is detachably mounted on said instrument body whereby it may be replaced by another similar staple carrier.

4. The structure claimed in claim 1 wherein said annular anvil plate is detachably mounted on said anvil whereby it may be replaced by another similar anvil plate.

5. The structure claimed in claim 1 including releasable safety means to prevent shifting of said staple driver actuator and said scalpel actuator until said safety means is released.

6. The structure claimed in claim 1 including more than one annular array of staples in said staple carrier together with a staple driver for each staple array.

7. The structure claimed in claim 6 wherein said staple carrier comprises a hollow cylindrical element, said staple carrier having a longitudinal slot therein for each of said staples of each array thereof, a staple being located within each of said slots, said staple drivers comprising concentric cylindrical elements each having a longitudinally extending leg slidably mounted in each of said staple carrier slots for its respective staple array, said staple carrier having an interior annular shoulder, each of said staple drivers having a plurality of tines adapted to contact said shoulder to limit the amount by which said staple drivers can be shifted by said staple driver actuator to prevent overforming of said staples, said cylindrical scalpel having a diameter such as to be in frictional engagement with the interior surface of said hollow cylindrical staple carrier and to be axially shiftable therein by said scalpel actuator.

8. The structure claimed in claim 1 including means to limit the amount by which said staple driver can be shifted by said staple driver actuator to prevent overforming of said staples.

9. The structure claimed in claim 1 wherein said staple carrier comprises a hollow cylindrical element, said staple carrier having a longitudinal slot therein for each of said staples of said at least one array, a staple being located within each of said slots, said staple driver comprising a cylindrical element having a longitudinally extending leg slidably mounted in each of said staple carrier slots, said staple carrier having an interior annular shoulder, said staple driver having a plurality of tines adapted to contact said shoulder to limit the amount by which said staple driver can be shifted by said staple driver actuator to prevent overforming of said staples, said cylindrical scalpel having a diameter such as to be in frictional engagement with the interior surface of said hollow cylindrical staple carrier and to be axially shiftable therein by said scalpel actuator.

10. The structure claimed in claim 1 wherein said surgical stapling instrument is substantially symmetrical about its long axis.

11. The structure claimed in claim 1 wherein said scalpel actuator comprises an elongated hollow element located within and axially shiftable within said instrument body, means to prevent rotation of said scalpel actuator about its long axis with respect to said instrument body, said staple driver actuator comprising an elongated hollow element located within said axially shiftable within said scalpel actuator, means to prevent rotation of said staple driver actuator about its long axis with respect to said scalpel actuator, said conical anvil having an elongated shank located within and axially shiftable within said staple driver actuator, and means to prevent rotation of said anvil shank about its long axis with respect to said staple driver actuator.

12. The structure claimed in claim 11 including means to prevent unintentional disassembly of said instrument, said last mentioned means comprising a stop pin mounted in coaxial perforations in said instrument body and extending transversely thereof and through corresponding longitudinal slots in said scalpel actuator, said staple driver actuator and said anvil shank.

13. The structure claimed in claim 11 wherein said means to shift said anvil comprises an anvil drive screw rotatably mounted at said proximal end of said instrument body, said anvil drive screw being threadedly engaged in an internally threaded axial bore in the free end of said anvil shank, said means to shift said staple driver actuator comprising a staple drive wheel captively and rotatably mounted on said instrument body near said proximal end thereof, said staple drive wheel having an internally threaded sleeve, a first split nut non-rotatably mounted on said instrument body and axially shiftable thereon, said first split nut being externally threaded and threadedly engaged with said internally threaded staple drive wheel sleeve, said first split nut having a pair of diametrically opposed lugs extending through longitudinal slots in said instrument body and into diametrically opposed openings in said staple driver actuator such that rotation of said staple drive wheel will result in axial shifting of said first split nut and said staple driver actuator, said means to shift said scalpel actuator comprises a scalpel drive wheel, said scalpel drive wheel being rotatably mounted on said staple drive wheel sleeve, said scalpel drive wheel having an internally threaded sleeve, a collar mounted on said instrument body and overlying said scalpel drive wheel sleeve, said collar and said staple drive wheel cooperating to prevent axial shifting of said scalpel drive wheel, a second split nut non-rotatably mounted on said instrument body and axially shiftable thereon, said second split nut being externally threaded and threadedly engaged with said internally threaded scalpel drive wheel sleeve, said second split nut having a pair of diametrically opposed lugs extending through longitudinal slots in said instrument body and into diametrically opposed openings in said scalpel actuator such that rotation of said scalpel drive wheel will result in axial shifting of said second split nut and said scalpel actuator.

14. The structure claimed in claim 13 including a first latch mounted on said instrument body, said first latch being shiftable between a first position wherein it is engaged in a notch in said staple drive wheel to prevent rotation thereof and a second position out of engagement with said staple drive wheel notch, means biasing said first latch to its first position, said first latch having a nose thereon engageable by said anvil shaft to shift said first latch from its first to its second position only when said anvil and anvil plate is spaced from said staple carrier by a distance within the forming limits of said staples, a second latch mounted on said scalpel drive wheel, said second latch being shiftable between a first position wherein it is engaged in a notch in said collar to prevent rotation of said scalpel drive wheel and a second position out of engagement with said collar notch, means biasing said second latch to its first position, said second latch having a nose thereon engagable by said first split nut to shift said second latch from its first to its second position when said staple driver actuator has been shifted to said staple driving position and said staples have been clinched by said anvil plate, whereby proper sequential operation of said surgical stapling instrument is assured.

15. The structure claimed in claim 14 including a safety pin removably mounted in coaxial perforations in said scalpel drive wheel, said sleeve of said staple drive wheel and said first split nut when said staple driver actuator and said scalpel actuator are in their respective retracted positions, whereby to prevent shifting of said staple driver actuator and said scalpel actuator until removal of said safety pin.

16. The structure claimed in claim 15 including means to prevent unintentional disassembly of said instrument, said last mentioned means comprising a stop pin mounted in coaxial perforations in said instrument body and extending transversely thereof and through corresponding longitudinal slots in said scalpel actuator, said staple driver actuator and said anvil shank.

17. The structure claimed in claim 1 wherein said sequence control means comprises a first latch means to prevent actuation of said staple driver actuator shifting means to shift said staple driver actuator to its staple driving position until said anvil and its anvil plate are spaced from said staple carrier by a distance within the forming limits of said staples, and second latch means to prevent actuation of said scalpel actuator shifting means to shift said scalpel actuator to its scalpel driving position until said staples have been clinched by said anvil plate.

* * * * *